(12) United States Patent
Martz et al.

(10) Patent No.: US 12,105,016 B2
(45) Date of Patent: *Oct. 1, 2024

(54) USING FI-RT TO BUILD WINE CLASSIFICATION MODELS

(71) Applicant: PENROSE HILL, Napa, CA (US)

(72) Inventors: Matthew K. Martz, Chapel Hill, NC (US); Philip James, New York, NY (US); Erik Steigler, New York, NY (US)

(73) Assignee: PENROSE HILL, Napa, CA (US)

( * ) Notice: Subject to any disclaimer, the term of this patent is extended or adjusted under 35 U.S.C. 154(b) by 319 days.

This patent is subject to a terminal disclaimer.

(21) Appl. No.: 17/589,234

(22) Filed: Jan. 31, 2022

(65) Prior Publication Data

US 2023/0243738 A1   Aug. 3, 2023

(51) Int. Cl.
| | | |
|---|---|---|
| *G01N 21/17* | (2006.01) | |
| *G06F 17/14* | (2006.01) | |
| *G06N 3/04* | (2023.01) | |
| *G06N 3/042* | (2023.01) | |
| *G06V 10/80* | (2022.01) | |
| *G06V 10/84* | (2022.01) | |

(52) U.S. Cl.
CPC .............. *G01N 21/17* (2013.01); *G06F 17/14* (2013.01); *G06N 3/042* (2023.01); *G06V 10/809* (2022.01); *G06V 10/85* (2022.01); *G01N 2021/1765* (2013.01)

(58) Field of Classification Search
CPC ........... G01N 21/17; G01N 2021/1765; G06V 10/809; G06V 10/85; G06N 3/042; G06F 17/14

See application file for complete search history.

(56) References Cited

U.S. PATENT DOCUMENTS

| | | | | |
|---|---|---|---|---|
| 2015/0247814 A1* | 9/2015 | Hofmann | ............... | G01N 24/08 324/307 |
| 2016/0091419 A1* | 3/2016 | Watson | .................. | G01N 33/02 356/407 |

FOREIGN PATENT DOCUMENTS

CN         113378971 A  *  9/2021  ............. G06N 3/045

* cited by examiner

*Primary Examiner* — Jamil Ahmed
(74) *Attorney, Agent, or Firm* — Buckley, Maschoff & Talwalkar LLC

(57) ABSTRACT

Some embodiments of the present disclosure relate to systems and methods including generating, by infrared spectroscopy, spectra data identifying quantities and associated wavelengths of radiation absorption for each of a plurality of wine samples as determined by the infrared spectroscopy; converting the spectra data for each wine sample to a set of discretized data; transforming the discretized data into a visual image representation of each respective wine sample, the visual image representation of each wine sample being an optically recognizable representation of the corresponding converted set of discretized data; and storing a record including the visual image representation of each wine sample in a memory.

18 Claims, 10 Drawing Sheets

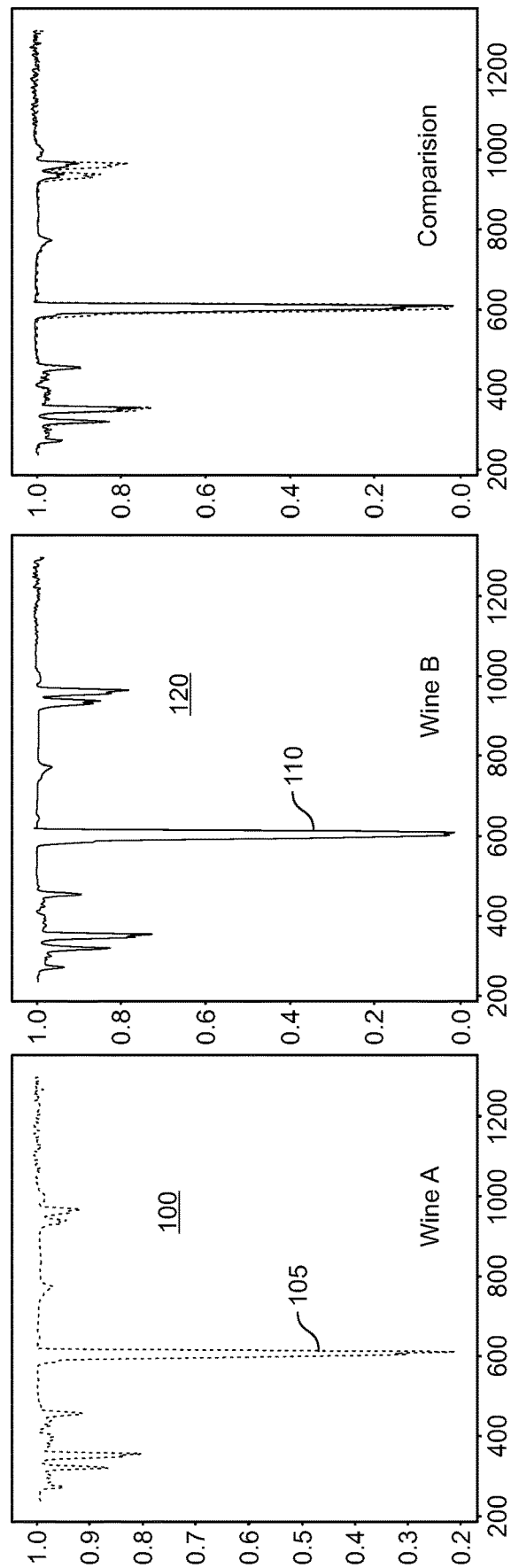

USING FI-RT TO BUILD WINE CLASSIFICATION MODELS

BACKGROUND

Conventionally, consumable items such as food and beverages, including wine for example, might be produced using well-established techniques and procedures. An expert knowledgeable of the items being produced might classify the quality of the produced items based on the expert's stated taste, smell, and feel of the items. Such evaluations of the produced items might be useful in determining, for example, the quality of the items, pricing for the items, suitable uses/markets for the items, compliance of the items with applicable regulatory and/or industry policies, etc. However, such evaluations are inextricably limited by the experience, availability, and personal preferences/biases of the "experts".

Some systems and processes have been developed to evaluate food and beverages using, at least in part, machine-based systems that might detect and/or categorize food and beverage samples based on calibrated measurements (e.g., chemical properties, etc.) provided using one or more different technologies. Some of the technologies used include, for example, mass spectrometry, gas chromatography, and other analytical tools and processes. A feature of at least some of these systems is that the machines and systems are calibrated to detect a particular chemical compound, where the particular chemical compound has one or more characteristic features that can be detected and identified by the calibrated system. However, a limitation of such systems is that the machine or system is calibrated to look for specific, known chemical compounds (e.g., percentage of alcohol in a wine sample).

Accordingly, it would therefore be desirable to provide a system and method to detect and classify samples, including samples for which the constituent chemical makeup thereof might not be known, in an efficient and data-driven manner.

BRIEF DESCRIPTION OF THE DRAWINGS

FIGS. 1A-1C are illustrative depictions of wave spectra graphs for wine samples;

Figures 2A, 2B, 2C:
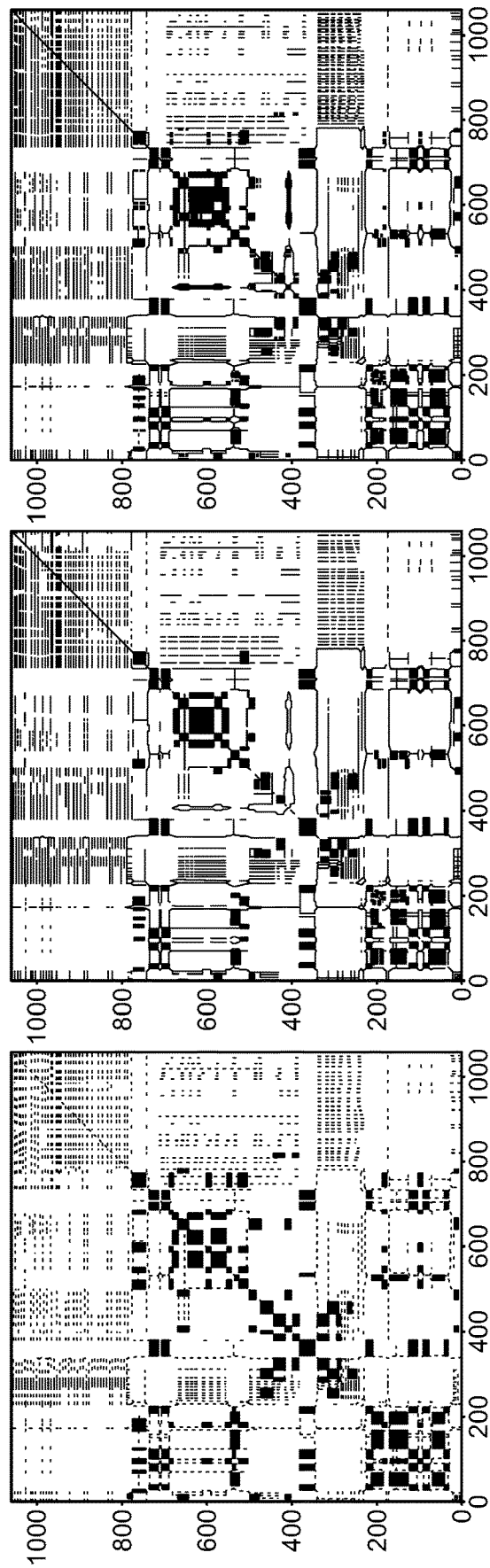
FIGS. 2A-2C are illustrative example depictions of a visual images derived from a conversion of the wave spectra graphs in FIGS. 1A-1C, respectively.

Throughout the drawings and the detailed description, unless otherwise described, the same drawing reference numerals will be understood to refer to the same elements, features, and structures. The relative size and depiction of these elements may be exaggerated or adjusted for clarity, illustration, and/or convenience.

DETAILED DESCRIPTION

In the following detailed description, numerous specific details are set forth in order to provide a thorough understanding of embodiments. However, it will be understood by those of ordinary skill in the art that the embodiments may be practiced without these specific details. In other instances, well-known methods, procedures, components and circuits have not been described in detail so as not to obscure the embodiments.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are system, method and/or computer program product embodiments, and/or combinations and sub-combinations thereof, to provide and support building (i.e., generating) a computer vision classification model or system that is trained using visual image representations (also referred to herein at various times simply as an images) derived or converted from raw spectroscopy data of an analyzed sample (e.g., a wine sample analyzed by infrared spectroscopy). In some embodiments, aspects of transfer learning might be applied to a pre-trained computer vision model, system, or algorithm to facilitate efficient training of the computer vision classification model or system using the image(s) of the wine sample. The present disclosure also provides system, method and/or computer program product embodiments, and/or combinations and sub-combinations thereof, to provide and support using a classification model or system as disclosed herein to provide a number and variety of practical applications. Some embodiments include use-cases related to, for example, a detection of environmental perturbations, determining customer cohort flavor profiles, categorizing and labeling of analyzed samples (e.g., wine samples), and other calculated, determined, and predictive outputs. Some embodiments of a classification model or system disclosed herein might use or leverage a pre-trained computer vision model, system, or algorithm implementing a neural network (e.g., a convolutional neural network, CNN) for computer vision that is pre-trained to perform one or more computer vision tasks (e.g., vision recognition, segmentation, classification, etc.).

FIGS. 1A-1C are illustrative depictions of example wave spectra graphs for wine samples analyzed by infrared spectroscopy, in accordance with some embodiments herein. As used herein, infrared spectroscopy generally refers to the measurement of the interaction of radiation in the infrared region of the electromagnetic spectrum with a sample of matter by absorption, emission, or reflection, based on the fact that molecules absorb frequencies that are characteristic of their structure. Infrared spectroscopy encompasses a range of measurement techniques. In some embodiments herein, Fourier-transform Infrared Spectroscopy (Fi-RT) might be the type of infrared spectroscopy measurement technique used to record infrared spectra where the Fourier transform is performed on the raw infrared spectroscopy data to obtain an output representing light output as a function of infrared wavelength (or its equivalent wave number). FIGS. 1A-1C are examples of infrared wave spectra graphs obtained using Fi-RT. The peaks in the wave spectra in FIGS. 1A-1C correspond to the region(s) where specific compound(s) the infrared spectroscopy machine is calibrated to detect are absorbing and exciting at a particular wavelength and its measured relative value. For example, the infrared spectroscopy machine might be calibrated to detect alcohol in a wine sample and the largest peak in FIGS. 1A and 1B (peak 105 and peak 110 respectively) might indicate the particular wavelength alcohol absorption is detected and its measured relative value.

As an example, FIG. 1A is an illustrative depiction of a wave spectra graph of a first wine sample (e.g., wine A) analyzed by Fi-RT, FIG. 1B is an illustrative depiction of a wave spectra graph of a second wine sample (e.g., wine B) analyzed by Fi-RT, and FIG. 1C is an illustrative depiction of a combined wave spectra graph where the wave spectra of the first wine sample and the second wine sample are depicted on the same graph. In some regions of the combined wave spectra graph of FIG. 1C, a portion of the wave spectra of the first wine sample and the wave spectra of the second wine sample have the same representative value(s), with one wave spectra being overlaid the other wave spectra. In other regions of the combined wave spectra graph of FIG. 1C, the wave spectra of the first wine sample and the wave spectra of the second wine sample are not consistent with each other. That is, FIG. 1C might provide or facilitate a comparison of the similarities and differences between the wave spectra of wine A and the wave spectra of wine B for detected chemical compounds.

As demonstrated by FIGS. 1A-1C, wave spectra might be used to effectively identify particular chemical compounds as represented by measurements at specific wavelengths (i.e., peaks). In some aspects, it may be desirable to use the full extent of the spectra data to, for example, classify, evaluate, compare, and other processes, of analyzed (wine) samples. For example, instead of comparing analyzed samples at particular wavelengths by machines designed to measure calibrated portions of the (infrared) spectrum, it may be beneficial to view and compare a full extent of the spectra for the (wine) samples. Use of the full spectra data might facilitate and support, for example, the detection (i.e., identifying) of unknown or unidentified chemical compounds, and chemical compounds not yet identified as being in a particular type of sample. For example, a technique that uses the full spectra of a (wine) sample might identify a chemical compound not previously identified as being present in wine or other sample being analyzed. The identification or detection of such unidentified chemical compounds might be beneficial in detecting flavor imbuing and/or other chemical compounds in an analyzed (wine) sample.

Some embodiments and examples herein may be discussed in the context of obtaining wave spectra of an analyzed sample using Fi-RT. It is noted that there are different types of infrared spectroscopy measurement techniques and embodiments herein might be implemented using other types of infrared spectroscopy, unless otherwise noted.

Different techniques might be used, for various practical purposes, to convert time series data into a visual image representation of the time series data. In some embodiments, the Markov transition fields (MTF) visualization technique might be used to convert or otherwise transform a set of time series data into a visual image representation (i.e., an image) of the set of time series data. Details of the MTF visualization technique are not the subject of the present disclosure and might include multiple process steps including, for example, discretizing the time series along the different values it can take, building a Markov transition matrix, computing transition probabilities, computing the Markov transition field, computing an aggregated MTF, extracting meaningful metrics, and mapping transition probabilities back to the initial signals. An important step of the MTF process is discretizing or binning an input signal (e.g., time series data) for the further process steps. In some embodiments herein, the spectra data for a (wine) sample might be converted to a set of discretized data as part of the MTF (or other) visualization process and further processed to generate an image representation of the full spectra data.

In some embodiments, the raw spectra data (e.g., the spectra data depicted in FIGS. 1A and 1B) might be processed, in essence, as time series data with the spectra data occurring over a particular wavelength occur over a time or over a distance.

FIGS. 2A-2C are illustrative example depictions of visual images derived from a conversion of the wave spectra graphs in FIGS. 1A-1C, respectively. The images in FIGS. 2A-2C include an image grid or matrix based on spectra time series. FIG. 2A is a visual image representation of the time series spectra of FIG. 1A, FIG. 2B is a visual image representation of the time series spectra of FIG. 1B, and FIG. 2C is an image representation of the combined time series spectra shown in FIG. 1C. Referring to FIG. 2C, some regions include pixels generated based on spectra strictly from either FIG. 1A or 1B. Those regions highlight differences between the two spectra 100 and 120. Some regions of FIG. 2C include a combination of pixels generated based on spectra from both FIGS. 1A and 1B, where the spectra overlay each other. For example, the image of FIG. 2C clearly illustrates there is significant overlay between these two time series as supported by the raw spectra data depicted in FIGS. 1A and 1B.

Figure 3:
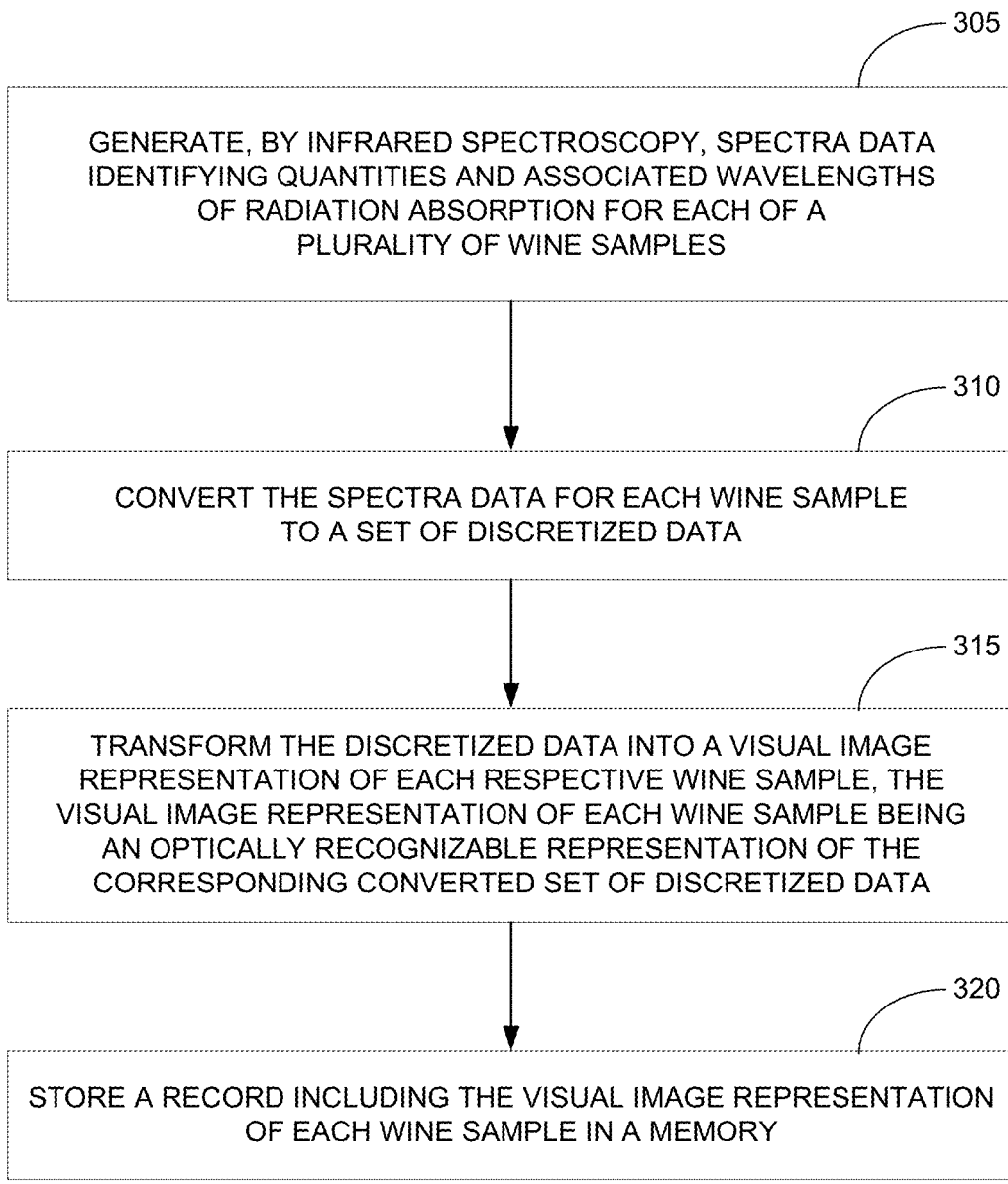
FIG. 3 is an illustrative flow diagram for a process, according to some embodiments.

FIG. 3 is an illustrative flow diagram for a process 300, according to some embodiments. At operation 305, spectra data is generated by infrared spectroscopy analysis of a sample (e.g., wine). The generated spectra data identifies quantities of chemical compound(s) and the associated wavelengths. FIGS. 1A and 1B are illustrative examples of the wave spectra graphs or diagrams that might be generated by Fi-RT spectroscopy in accordance with some embodiments of the present disclosure.

At operation 310, the spectra data generated in operation 305 is converted or otherwise processed to a set of discretized data. In some aspects the converting of the spectra data to discretized data facilitates and supports processing the spectra data as time series. Operation 315 further transforms the discretized data into a visual image representation of the full spectra of the analyzed (wine) sample. In some aspects, the visual image representation of the full spectra of the analyzed sample is an optically recognizable representation of the corresponding set of discretized data. As used herein, optically recognizable refers to an image that is machine readable by a computer vision system, including but not limited to a computer vision system including a machine learning model, algorithm, or network.

In some embodiments, operation 315 might include a MTF process. In some embodiments, operations 310 and 315 might comprise separate steps of a process (e.g., MTF), separate steps of different processes, or even be combined as one step of a common process (e.g., MTF or some other image visualization process or technique).

At operation 320, a record or other data structure including the visual image representation of the spectra for the analyzed sample (e.g., wine sample) may be stored in a memory device or system. The image of the spectra for the analyzed sample might be stored in the memory for further processing, including, for example, one or more of the other processes disclosed hereinbelow.

Figure 4:
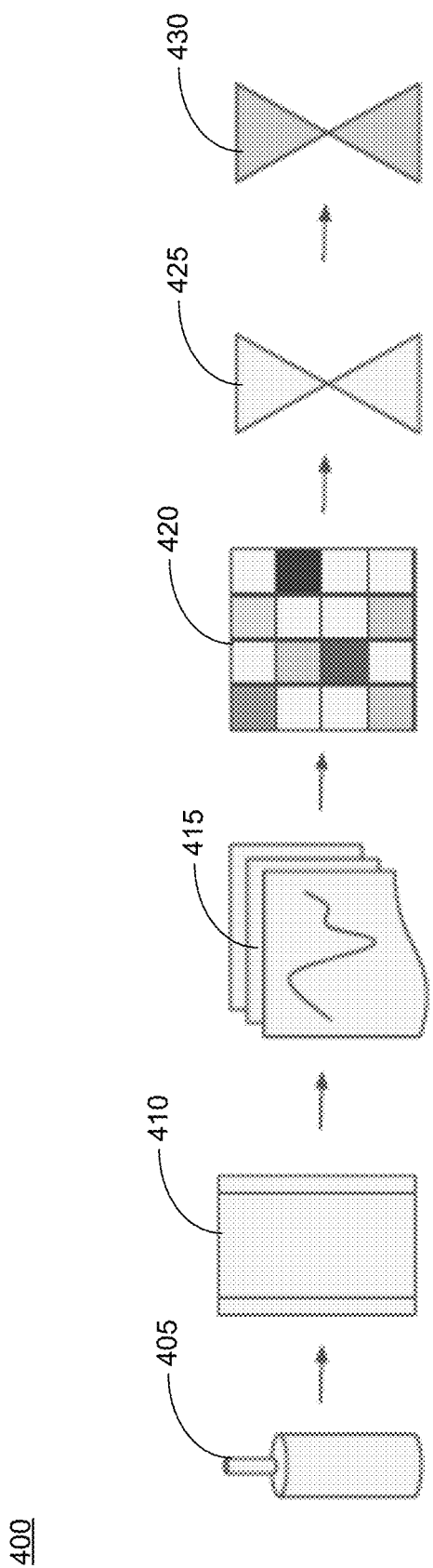
FIG. 4 is an illustrative depiction of an example processing pipeline for training a computer vision system, in accordance with some embodiments.

FIG. 4 is an illustrative depiction of an example processing pipeline 400 for training a computer vision system, in accordance with some embodiments. Referring to FIG. 4, a beverage such as wine for example, may be analyzed by an infrared spectroscopy system (e.g., Fi-RT) 410 to produce spectra data 415 representative of each analyzed wine (or other) sample. The (raw) spectra data 415 for each sample is converted, transformed, or otherwise processed into a visual image representation 420 by a visualization process or algorithm (e.g., MTF).

The output of the visualization process, that is the images corresponding to the spectra data, are provided to a pre-trained computer vision model, system, or network 425. In some aspects, the images 420 include images associated with at least one specified classification. As an example, a classification category might be environmental perturbations including the specified classifications of, for example, smoke taint, drought, blight, soil contamination, and other environmental conditions that might (or might not) imbue a flavor to a sample wine at some point in the production of the wine.

As used herein, pre-trained computer vision model 425 has been previously (i.e., pre-) trained to perform one or more visualization tasks related to computerized vision systems such as, for example, tasks or methods for object detection, image classification, visual relationship detection, image reconstruction, instance and semantic segmentation, etc. In some aspects, the pre-trained computer vision model 425 uses process(es) such as "transfer learning" to leverage knowledge of the pre-trained computer vision model 425 gained thereby learning to perform its designed tasks to further generate a trained computer vision classification model, system, or network 430.

In some aspects, the combination of the pre-trained computer vision model 425 and the application or use of transfer learning thereby enables and supports the generation of the trained computer vision classification model 430 based on even a limited number of images 420. For example, Applicant has realized a well performing trained computer vision classification model, system, or network 430 using about ten (10) images provided as input to a pre-trained computer vision model that further uses transfer learning to build the trained computer vision classification model.

The trained computer vision classification model, system, or network 430 is trained to visually detect and classify images consistent with the at least one specified classification associated with the images 420 provided as input(s) to the pre-trained computer vision model 425 to generate or build the trained computer vision classification model, system, or network 430.

Figure 5:
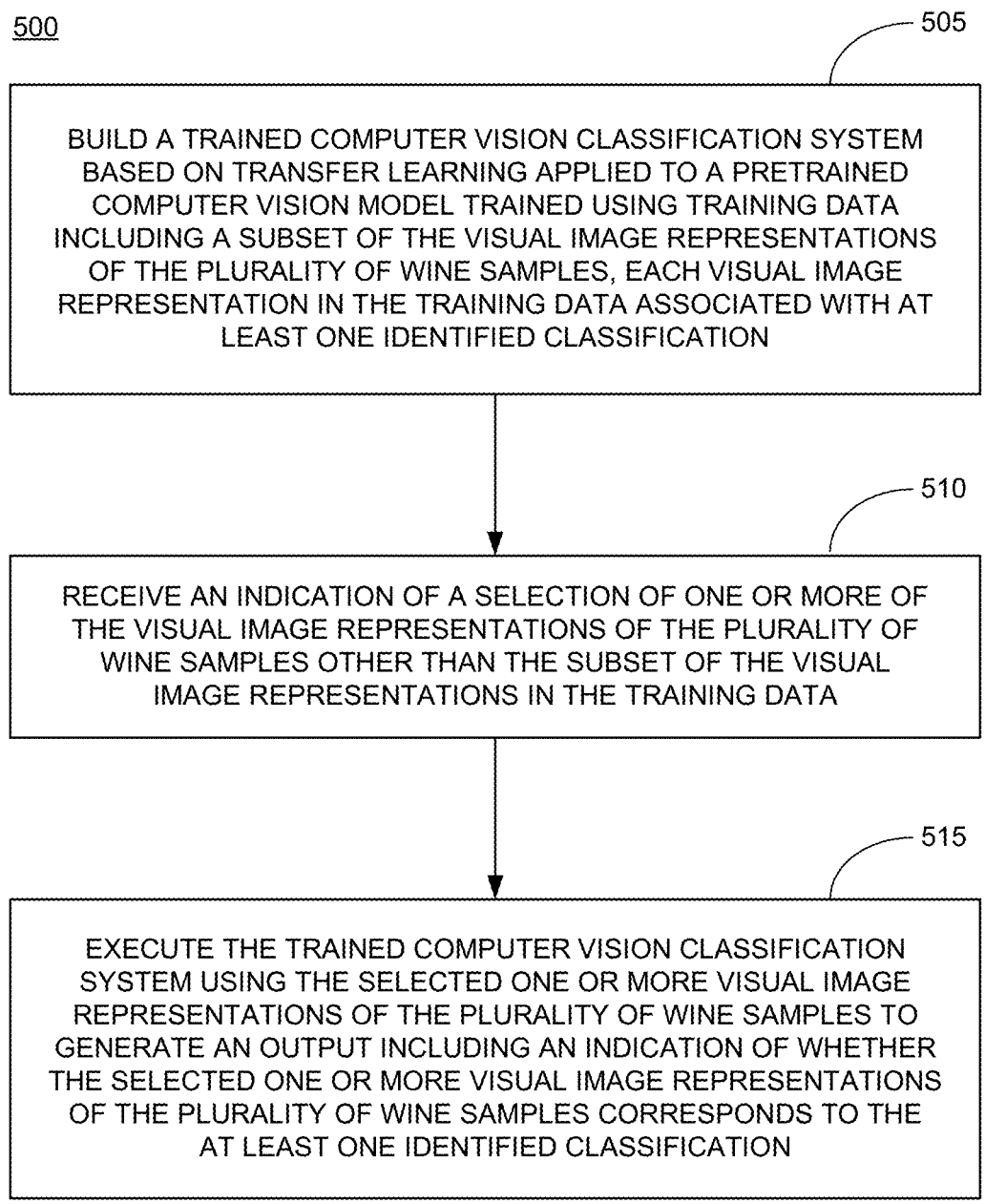
FIG. 5 is an illustrative flow diagram for a process, according to some embodiments.

FIG. 5 is an illustrative flow diagram for a process 500, according to some embodiments. In some aspects, process 500 relates to building and using a trained computer vision classification system. At operation 505, a trained computer vision classification system is built or otherwise generated. In some embodiments, the trained computer vision classification system may be built based on transfer learning applied to a pretrained computer vision model trained using training data including visual image representations of a plurality of wine samples, where each of the visual image representation in the training data is associated with at least one identified classification (e.g., environmental perturbations). In some embodiments, the trained computer vision classification system or model might be built as disclosed in FIG. 4.

Continuing to operation 510, an indication of a selection of one or more visual image representations of a plurality of wine samples may be received from a user (e.g., a person involved in the making of wine, not necessarily an expert winemaker). In some embodiments, the selected one or more visual images might be generated as disclosed in process 300 of FIG. 3. In some aspects, the images selected in operation 510 might not include the images used in training the trained computer vision classification system built in operation 505.

At operation 515, the trained computer vision classification model, system, or algorithm is executed using the selected one or more visual image representations of the plurality of wine samples to generate an output including an indication of whether the selected one or more images of the plurality of wine samples correspond to the at least one specified classification (e.g., one of the specified classifications of environmental perturbations).

In some embodiments, a wine sample might be obtained at any point in a wine production process. For example, a small sample of a wine very early in the wine making process (e.g., a sample of bulk juice) might be obtained and tested in accordance with one or more methods herein to ascertain whether the sample includes any detectable environmental perturbations. In this manner, an informed decision might be made whether to (or not to) purchase the bulk juice for winemaking purposes because it is, for example, smoke tainted, even though a conventional tasting or other chemical compound screening of the bulk juice might not detect any smoke taint.

In some aspects, processes disclosed herein might provide a mechanism for the detection and identification of specified classification(s) based on verifiable data. In contrast to identifications and detections based on the palate of a wine taster or other "expert" personnel, processes disclosed herein provide the benefit of being efficient, data-driven, and robust (e.g., repeatable).

Figure 6:
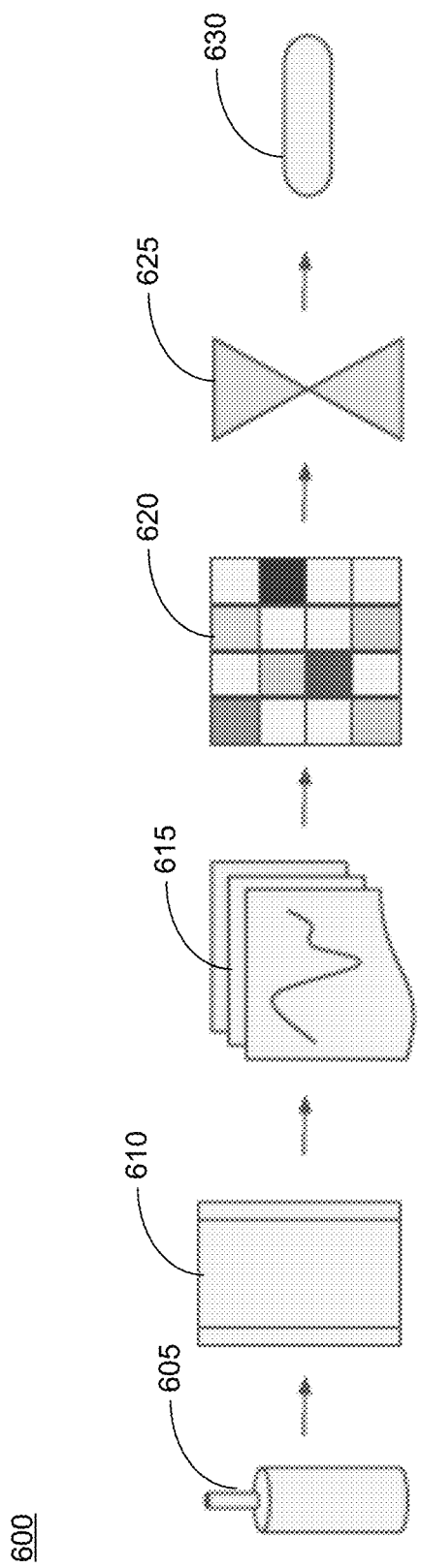
FIG. 6 is an illustrative depiction of an example processing pipeline for using a trained computer vision system, in accordance with some embodiments.

FIG. 6 is an illustrative depiction of an example processing pipeline 600 for using a trained computer vision system, in accordance with some embodiments. Continuing the example where the classification category is environmental perturbations including the specified classifications of, for example, smoke taint, drought, blight, soil contamination, and other environmental conditions, a trained model, system, or network built in accordance with the present disclosure might be able to detect whether there is, for example, any smoke taint, soil contamination, whether the grapes were grown in a certain degree of drought conditions, microbial contamination, and other specific environmental perturbations in an analyzed wine sample 605. Wine sample 605 is analyzed by an infrared spectroscopy system (e.g., Fi-RT) 610 to produce spectra data 615 representative of the analyzed wine (or other) sample. The spectra data 615 is converted or otherwise processed into a visual image representation 620 by a visualization process or algorithm (e.g., MTF). Image 620 is provided as an input to the trained computer vision classification model, system, or network 625 that processes the image to generate an output including an indication of whether the visual image representation of the wine sample 605 corresponds to at least one of the specified environmental perturbations. For example, the trained computer vision classification model, system, or network 625 might generate an output including an indication that moderate levels of soil contamination were detected in wine sample 605, with a 95% confidence level. Other formats of data might be produced by a trained computer vision classification model or network herein, other than the specific embodiment of the present example.

In some embodiments, a trained computer vision classification model, system, or network herein might be configured to proceed from a particular classification to a regression where the trained computer vision classification model, system, or network might provide an output of a level or severity (e.g., minimal, moderate, or severe) of the particular classification.

In some embodiments, processes and systems disclosed herein might be adapted, configured, and applied to a wide variety of different classification categories other than the example environmental perturbations category discussed above. For example, instead of detecting environmental perturbations, systems and processes herein might be configured to build transfer learning computer vision network systems similar to those disclosed in FIGS. 4 and 6, but configured to determine, for example, customer cohort flavor profiles for (wine) samples using infrared spectroscopy. In this example, a computer vision classification network or system may be built and trained using images associated with one or more particular customer flavor cohorts (i.e., groupings of customers having similar wine preference(s)), where particular wines perform well for particular cohort(s) and several cohorts comprise the specified classifications. Accordingly, the specified classifications might include, as an example, cohorts 1, 2, and 3, where these cohorts might be based on, for example, finance information/data, region, and some kind of demographic, etc. In an example use-case or application where the computer vision network system is trained using images associated with specified classifications of customer flavor cohorts 1, 2, and 3, a new wine (i.e., a wine not included in the training data for the computer vision network system) might be analyzed by infrared spectroscopy to obtain a visual image representation for that wine. The thus obtained image may then be processed through the trained computer vision classification network or system to determine which customer cohort this particular wine, as represented by the visual image representation thereof, will be classified. The techniques used to determine the customer flavor cohorts or other specified classifications for use with the systems and processes herein are independent of the present disclosure.

Figure 7:
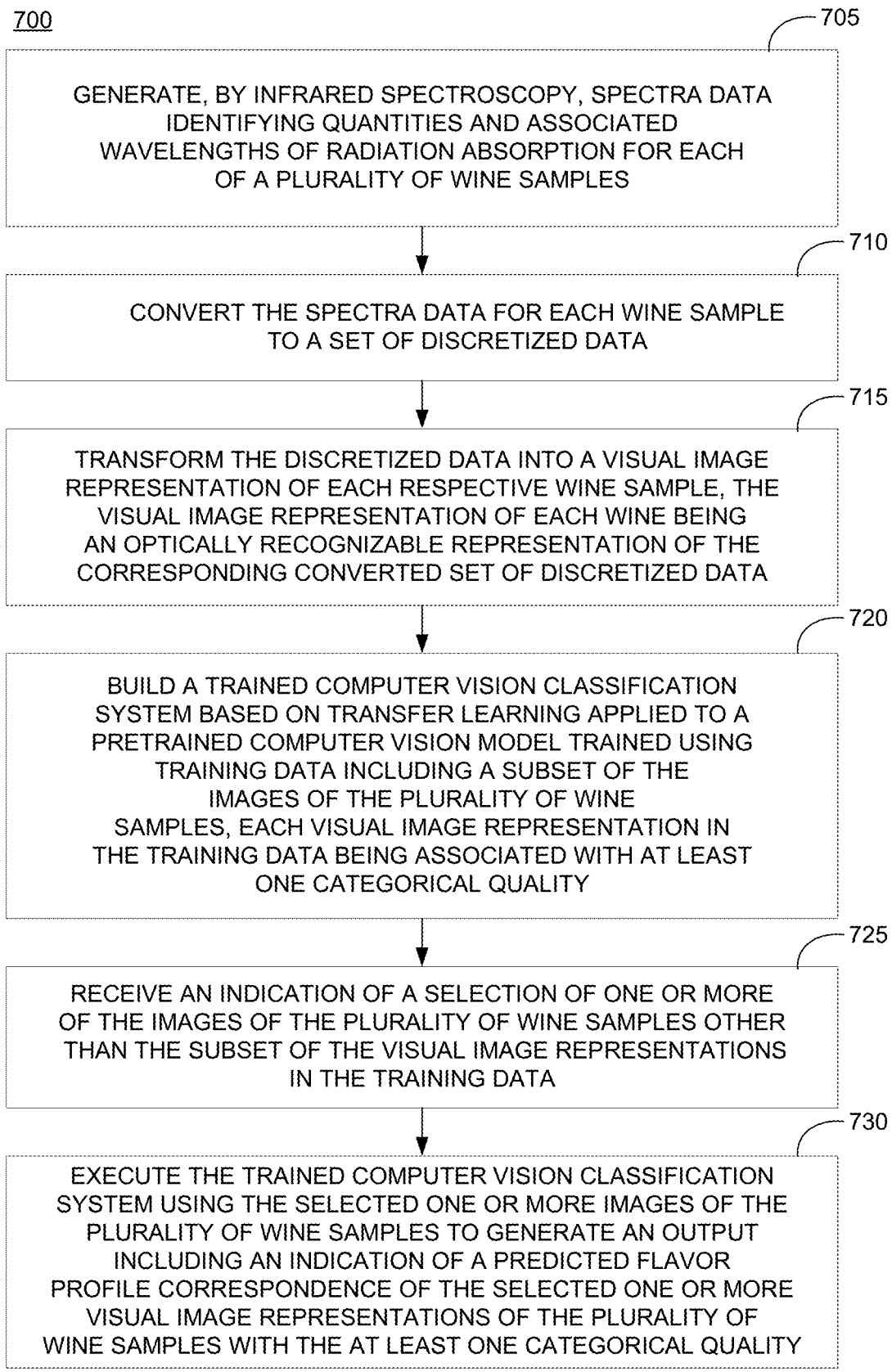
FIG. 7 is an illustrative flow diagram for a process, according to some embodiments.

FIG. 7 is an illustrative flow diagram for a process 700, according to some embodiments. At operation 705 spectra data identifying quantities and associated wavelengths of radiation absorption for each of a plurality of wine samples are generated by infrared spectroscopy. At operation 710, the spectra data obtained at operation 705 for each wine sample is converted to a set of discretized data to, for example, facilitate processing as time series. Continuing to operation 715, the discretized data may be transformed into a visual image representation of each respective wine sample. In some aspects, the visual image representation of each wine is an optically recognizable representation of the corresponding converted set of discretized data. At operation 720, a trained computer vision classification system is built based on transfer learning applied to a pretrained computer vision model trained using training data including a subset of the visual image representations of the plurality of wine samples, where each visual image representation in the training data is associated with at least one categorical quality. Proceeding to operation 725, an indication of a selection of one or more of the visual image representations of the plurality of wine samples other than the subset of the visual image representations used in the training data is received (for example, from a user). At operation 730, the trained computer vision classification system is executed using the selected one or more images of the plurality of wine samples to generate an output. The generated output might include an indication of a predicted flavor profile correspondence of the selected one or more images of the plurality of wine samples with the at least one categorical quality. In this manner, process 700 might relate to a process to categorize and label wine as a particular classification of wine using infrared spectroscopy.

Figure 8:
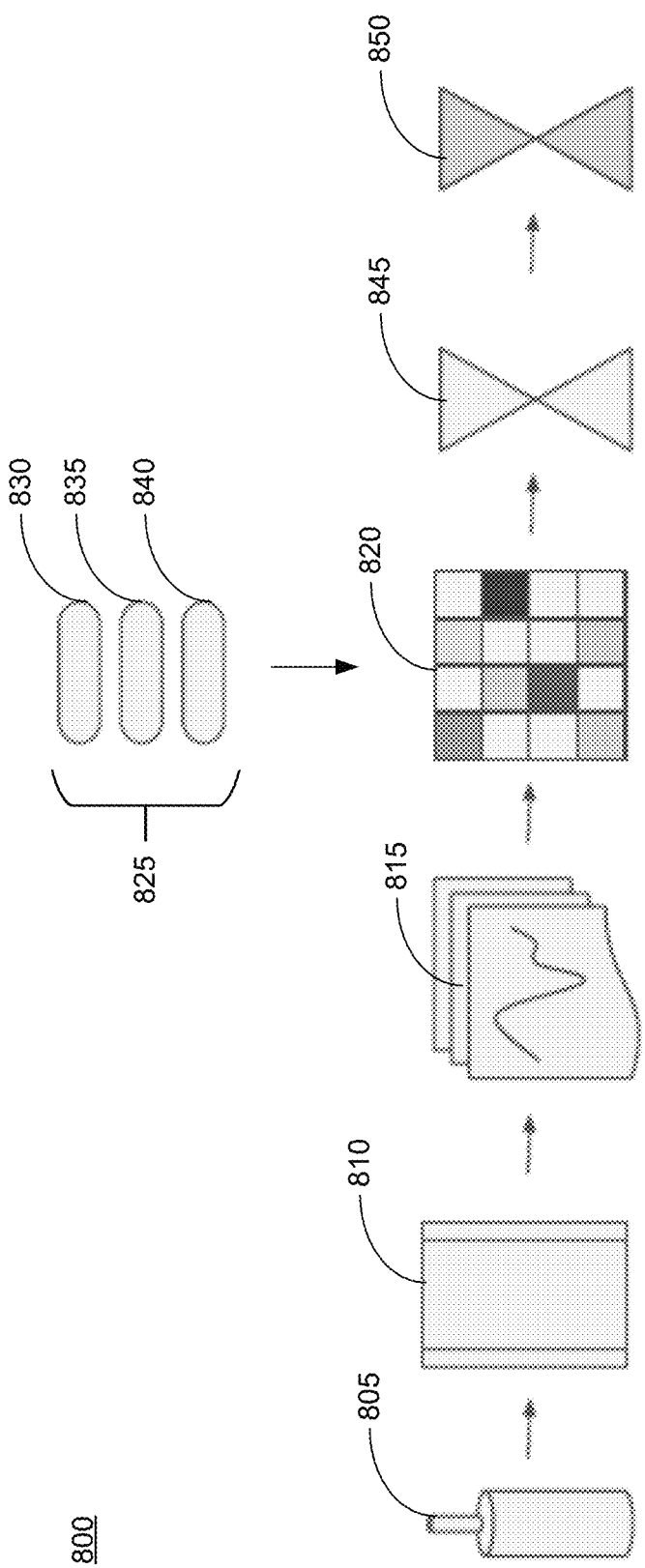
FIG. 8 is an illustrative depiction of an example processing pipeline for training a computer vision system, in accordance with some embodiments.
Figure 9:
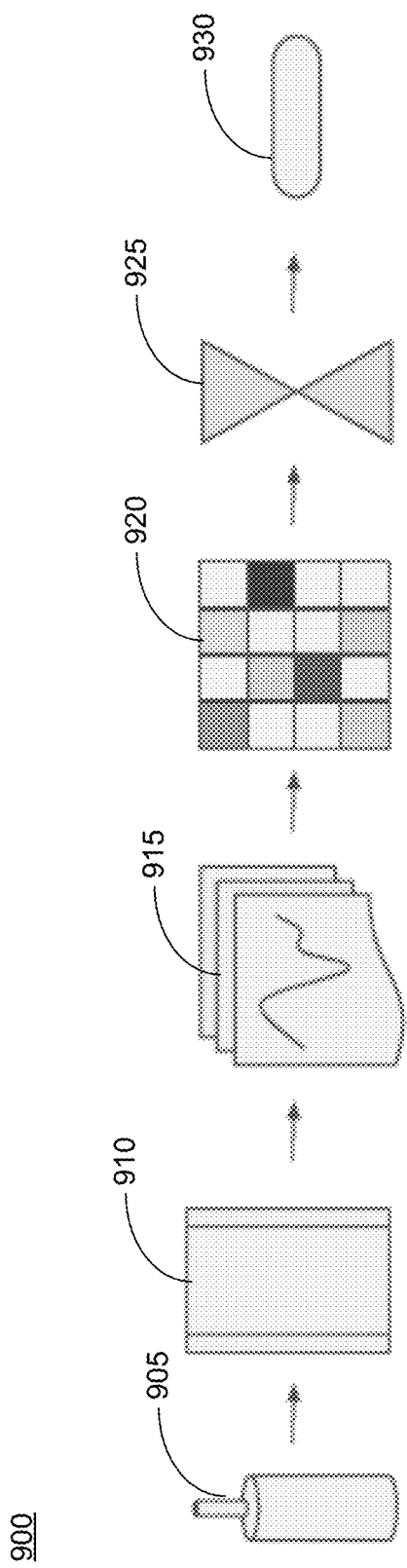
FIG. 9 is an illustrative depiction of an example processing pipeline for using a trained computer vision system, in accordance with some embodiments.

FIGS. 8 and 9 relate to aspects of process 700. FIG. 8 is an illustrative depiction of an example processing pipeline 800 for training a computer vision system, in accordance with some embodiments. Some aspects of FIG. 8 are at least similar to aspects of FIG. 4. As such, certain aspects common to FIGS. 4 and 8 might not be repeated in the discussion of FIG. 8. Referring to FIG. 8, a wine sample 805 may be analyzed by an infrared spectroscopy system (e.g., Fi-RT) 810 to produce spectra data 815 that is representative of each analyzed wine (or other) sample. The spectra data 815 for each sample is converted, transformed, or otherwise processed into a visual image representation 820 by a visualization process or algorithm (e.g., MTF).

FIG. 8 further includes human labeling inputs 825. The human labeling inputs might be provided, for example, by expert winemakers that label wine samples 805 by categorical qualities 830, 835, and 840. In the present example, categorical qualities 830 include environmental perturbation classifications, similar to those discussed hereinabove. Categorical qualities 835 might include marketing key performance indicators (KPIs) classifications such as, for example, grouping of wines based on a specified long term value (LTV) (e.g., high LTV versus low LTV), customer cohorts, one or more kinds of high value action groupings of wines, and cohort performance (e.g., refers to whether a particular wine will do well with a particular cohort or not, and maybe which cohort that will be more preferential for a particular win). Categorical qualities 840 might include categorical assignment classifications that refer to, for example, whether a wine or group of wines will fit particular flavor profiles or regionalities or varietals.

The human labeling may be used, in combination with transfer learning applied to pre-trained network or model 845, to generate or build trained computer vision classification model, system, or network (e.g., based in some embodiments on machine learning, such as a deep learning convolutional neural network) 850 that is trained to recognize and understand the different categorical quality classification, as specified in the human labeled images.

In some embodiments, a control set of data might be used in training the computer vision classification model, system, or network for the environmental perturbations. For other types of training data (e.g., marketing KPI's, categorical assignments, etc.), a control set may or may not be provided.

In some embodiments, the categorical quality classifications 825 might represent three different wines that were rated by a customer or other person. These customer-rated wines might be used by the pre-trained computer vision network 845 to understand what customers are drinking and preferring. In this manner, a flavor profile might be developed for user(s) through images. Furthermore, wine recommendations might be determined based on these new flavor profiles.

FIG. 9 is an illustrative depiction of an example processing pipeline 900 for using a trained computer vision system such as the trained computer vision classification model, system, or network 850 of FIG. 8, in accordance with some embodiments. Some aspects of FIG. 9 are at least similar to aspects of FIG. 6. As such, certain aspects common to FIGS. 6 and 9 might not be repeated in the discussion of FIG. 9. For example, wine sample 905 is analyzed by an infrared spectroscopy system 910 to produce spectra data 915 representative of the analyzed wine (or other) sample. The spectra data 915 is converted or otherwise processed into a visual image representation 920 by a visualization process or algorithm. Image 920 is further provided as an input to the trained computer vision classification model or network 925 that processes images to generate an output including an indication of a predicted flavor profile correspondence of the visual image representation of wine sample 905 with one of the categorical quality classifications 825.

Figure 10:
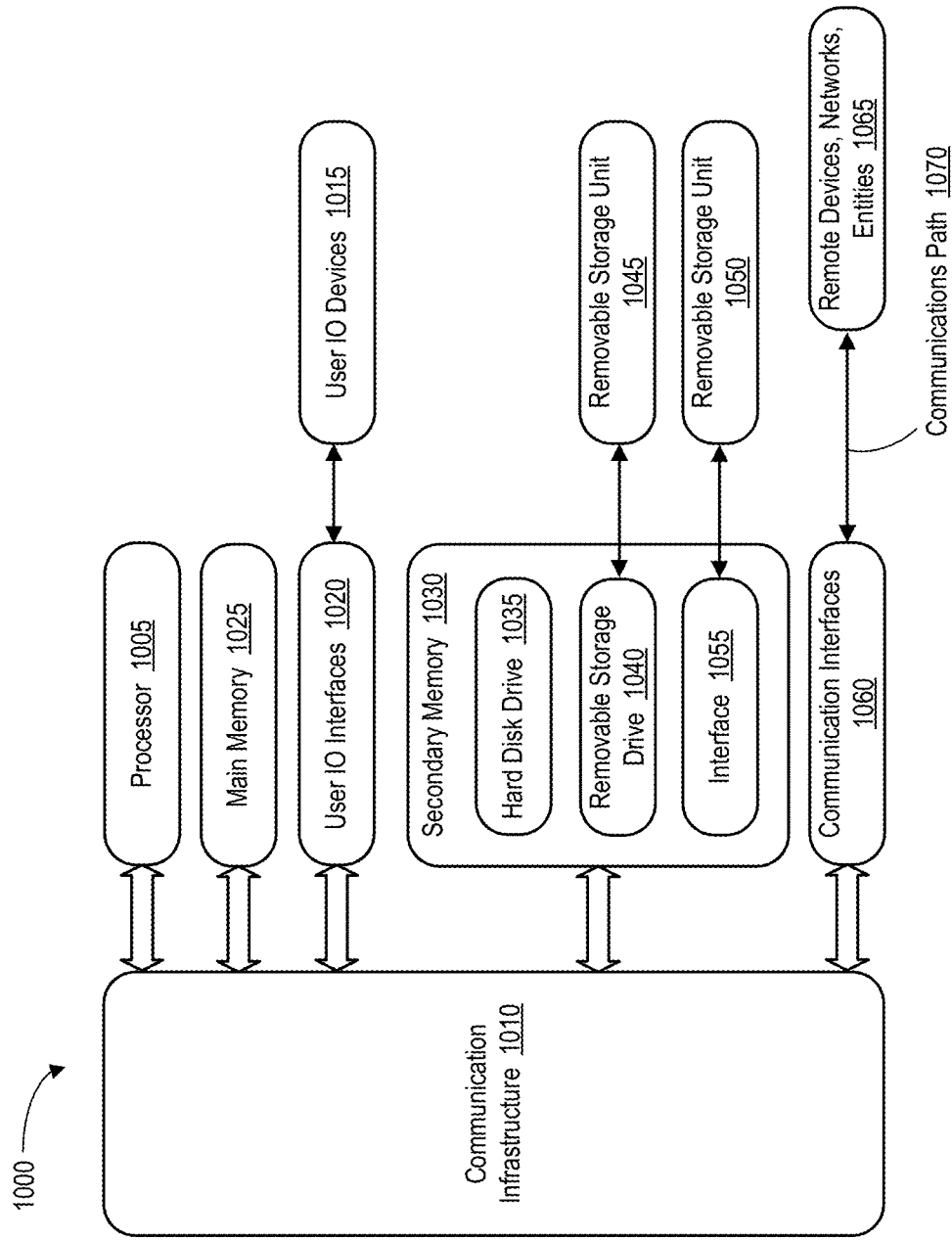
FIG. 10 is illustrative example of a computing system for use in some example embodiments disclosed herein.

Various embodiments can be implemented, for example, using one or more well-known computer systems, such as computer system 1000 shown in FIG. 10. The computer system 1000 can be any well-known computer capable of performing the functions described herein. Computer system 1000 includes one or more processors (also called CPUs), such as a processor 1005. Processor 1005 is connected to a communication infrastructure or bus 1010.

One or more processors 1005 may each be a Graphics Processing Unit ("GPU"). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1000 also includes user input/output device(s) 1015, such as monitors, keyboards, pointing devices, etc., that communicate with communication infrastructure xx010 through user input/output interface(s) 1020.

Computer system 1000 also includes a main or primary memory 1025, such as Random-Access Memory ("RAM"). Main memory 1025 may include one or more levels of cache. Main memory 1025 has stored therein control logic (i.e., computer software) and/or data.

Computer system 1000 may also include one or more secondary storage devices or memory 1030. Secondary memory 1030 may include, for example, a hard disk drive 1035 and/or a removable storage device or drive 1040. Removable storage drive 1040 may be a floppy disk drive, a magnetic tape drive, a compact disk drive, an optical storage device, tape backup device, and/or any other storage device/drive.

Removable storage drive 1040 may interact with a removable storage unit 1045. Removable storage unit 1045 includes a computer usable or readable storage device having stored thereon computer software (control logic) and/or data. Removable storage unit 1045 may be a floppy disk, magnetic tape, compact disk, DVD, optical storage disk, and/any other computer data storage device. Removable storage drive 1040 reads from and/or writes to removable storage unit 1045 in a well-known manner.

According to an exemplary embodiment, secondary memory 1030 may include other means, instrumentalities or other approaches for allowing computer programs and/or other instructions and/or data to be accessed by computer system 1000. Such means, instrumentalities or other approaches may include, for example, a removable storage unit 1050 and an interface 1055. Examples of the removable storage unit 1050 and the interface 1055 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1000 may further include a communication or network interface 1060. Communication interface 1060 enables computer system 1000 to communicate and interact with any combination of remote devices, remote networks, remote entities, etc. (individually and collectively referenced by reference number 1065). For example, communication interface 1060 may allow computer system 1000 to communicate with remote devices 1065 over communications path 1070, which may be wired and/or wireless, and which may include any combination of LANs, WANs, the Internet, etc. Control logic and/or data may be transmitted to and from computer system 1000 via communication path 1070.

In an embodiment, a tangible apparatus or article of manufacture comprising a tangible computer useable or readable medium having control logic (software) stored thereon is also referred to herein as a computer program product or program storage device. This includes, but is not limited to, computer system 1000, main memory 1025, secondary memory 1030, and removable storage units 1045 and 1050, as well as tangible articles of manufacture embodying any combination of the foregoing. Such control logic, when executed by one or more data processing devices (such as computer system 1000), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 10. In particular, embodiments may operate with software, hardware, and/or operating system implementations other than those described herein.

Although specific hardware and data configurations have been described herein, note that any number of other configurations may be provided in accordance with some embodiments of the present invention (e.g., some of the information associated with the databases and storage elements described herein may be combined or stored in external systems). Moreover, although some embodiments are focused on particular types of applications and services, any of the embodiments described herein could be applied to other types of applications and services. In addition, the displays shown herein are provided only as examples, and any other type of user interface could be implemented.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims Various embodiments can be implemented, for example, using one or more well-known computer systems, such as computer system 1000 shown in FIG. 10. The computer system 1000 can be any well-known computer capable of performing the functions described herein. Computer system 1000 includes one or more processors (also called CPUs), such as a processor 1005. Processor 1005 is connected to a communication infrastructure or bus 1010.

One or more processors 1005 may each be a Graphics Processing Unit ("GPU"). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1000 also includes user input/output device(s) 1015, such as monitors, keyboards, pointing devices, etc., that communicate with communication infrastructure xx06 through user input/output interface(s) 1020.

Computer system 1000 also includes a main or primary memory 1025, such as Random-Access Memory ("RAM"). Main memory 1025 may include one or more levels of cache. Main memory 1025 has stored therein control logic (i.e., computer software) and/or data.

Computer system 1000 may also include one or more secondary storage devices or memory 1030. Secondary memory 1030 may include, for example, a hard disk drive 1035 and/or a removable storage device or drive 1040. Removable storage drive 1040 may be a floppy disk drive, a magnetic tape drive, a compact disk drive, an optical storage device, tape backup device, and/or any other storage device/drive.

Removable storage drive 1040 may interact with a removable storage unit 1045. Removable storage unit 1045 includes a computer usable or readable storage device having stored thereon computer software (control logic) and/or data. Removable storage unit 1045 may be a floppy disk, magnetic tape, compact disk, DVD, optical storage disk, and/any other computer data storage device. Removable storage drive 1040 reads from and/or writes to removable storage unit 1045 in a well-known manner.

According to an exemplary embodiment, secondary memory 1030 may include other means, instrumentalities or other approaches for allowing computer programs and/or other instructions and/or data to be accessed by computer system 1000. Such means, instrumentalities or other approaches may include, for example, a removable storage unit 1050 and an interface 1055. Examples of the removable storage unit 1050 and the interface 1055 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1000 may further include a communication or network interface 1060. Communication interface 1060 enables computer system 1000 to communicate and interact with any combination of remote devices, remote networks, remote entities, etc. (individually and collectively referenced by reference number 1065). For example, communication interface 1060 may allow computer system 1000 to communicate with remote devices 1065 over communications path 1070, which may be wired and/or wireless, and which may include any combination of LANs, WANs, the Internet, etc. Control logic and/or data may be transmitted to and from computer system 1000 via communication path 1070.

In an embodiment, a tangible apparatus or article of manufacture comprising a tangible computer useable or readable medium having control logic (software) stored thereon is also referred to herein as a computer program product or program storage device. This includes, but is not limited to, computer system 1000, main memory 1025, secondary memory 1030, and removable storage units 1045 and 1050, as well as tangible articles of manufacture embodying any combination of the foregoing. Such control logic, when executed by one or more data processing devices (such as computer system 1000), causes such data processing devices to operate as described herein.

Based on the teachings contained in this disclosure, it will be apparent to persons skilled in the relevant art(s) how to make and use embodiments of the invention using data processing devices, computer systems and/or computer architectures other than that shown in FIG. 10. In particular, embodiments may operate with software, hardware, and/or operating system implementations other than those described herein.

Although specific hardware and data configurations have been described herein, note that any number of other configurations may be provided in accordance with some embodiments of the present invention (e.g., some of the information associated with the databases and storage elements described herein may be combined or stored in external systems). Moreover, although some embodiments are focused on particular types of applications and services, any of the embodiments described herein could be applied to other types of applications and services. In addition, the displays shown herein are provided only as examples, and any other type of user interface could be implemented.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A computer-implemented method, the method comprising:
generating, by infrared spectroscopy, spectra data identifying quantities and associated wavelengths of radiation absorption for each of a plurality of wine samples as determined by the infrared spectroscopy;
converting the spectra data for each wine sample to a set of discretized data;
transforming the discretized data into a visual image representation of each respective wine sample, the visual image representation of each wine being an optically recognizable representation of the corresponding converted set of discretized data;
storing a record including the visual image representation of each wine sample in a memory;
building a trained computer vision classification system, the trained computer vision classification system being built based on transfer learning applied to a pretrained computer vision model trained using training data including a subset of the visual image representations of the plurality of wine samples, each visual image representation in the training data associated with at least one identified classification;
receiving an indication of a selection of one or more of the visual image representations of the plurality of wine samples other than the subset of the visual image representations in the training data; and
executing the trained computer vision classification system using the selected one or more visual image representations of the plurality of wine samples to generate an output including an indication of whether the selected one or more visual image representations of the plurality of wine samples corresponds to the at least one identified classification.

2. The method of claim 1, wherein the infrared spectroscopy includes Fourier transform infrared spectroscopy.

3. The method of claim 1, wherein the transforming of the discretized data includes a Markov transition fields (MTF) analysis.

4. The method of claim 1, wherein the output includes an indication of a relative severity of the at least one identified environmental perturbation.

5. The method of claim 1, wherein the at least one identified classification includes one or more of an environmental perturbation classification, a customer cohort classification, and another type of classification.

6. A computer-implemented method, the method comprising:
generating, by infrared spectroscopy, spectra data identifying quantities and associated wavelengths of radiation absorption for each of a plurality of wine samples as determined by the infrared spectroscopy;
converting the spectra data for each wine sample to a set of discretized data;
transforming the discretized data into a visual image representation of each respective wine sample, the visual image representation of each wine being an optically recognizable representation of the corresponding converted set of discretized data;
building a trained computer vision classification system, the trained computer vision classification system being built based on transfer learning applied to a pretrained computer vision model trained using training data including a subset of the visual image representations of the plurality of wine samples, each visual image representation in the training data being associated with at least one categorical quality;
receiving an indication of a selection of one or more of the visual image representations of the plurality of wine samples other than the subset of the visual image representations in the training data; and
executing the trained computer vision classification system using the selected one or more visual image representations of the plurality of wine samples to generate an output including an indication of a predicted flavor profile correspondence of the selected one or more visual image representations of the plurality of wine samples with the at least one categorical quality.

7. The method of claim 6, wherein the at least one categorical quality associated with each visual image representation in the training data is provided by at least one of a machine-based expert system and a human.

8. The method of claim 6, wherein the infrared spectroscopy includes Fourier transform infrared spectroscopy.

9. The method of claim 6, wherein the transforming of the discretized data includes a Markov transition fields (MTF) analysis.

10. The method of claim 6, wherein the at least one categorical quality includes one or more environmental perturbations, one or more marketing key performance indicators, and one or more other types of categorical assignments related to wine.

11. The method of claim 6, wherein the at least one categorical quality includes one or more environmental perturbations and the training data includes a control set of data having at least one visual image representation of a wine sample without any known type of environmental perturbation.

12. The method of claim 6, wherein the at least one categorical quality includes one or more different user wine preferences and wherein the trained computer vision classification system is executed using the selected one or more visual image representations of the plurality of wine samples to generate an output including an indication of whether the selected one or more visual image representations of the plurality of wine samples corresponds to a user flavor profile consistent with the one or more different user wine preferences.

13. A system comprising:
a processor;
a storage device; and
a memory in communication with the processor, the memory storing program instructions, the processor operative with the program instructions to perform the operations of:
generating, by infrared spectroscopy, spectra data identifying quantities and associated wavelengths of radiation absorption for each of a plurality of wine samples as determined by the infrared spectroscopy;
converting the spectra data for each wine sample to a set of discretized data;
transforming the discretized data into a visual image representation of each respective wine sample, the visual image representation of each wine being an optically recognizable representation of the corresponding converted set of discretized data;
storing a record including the visual image representation of each wine sample in a memory;
building a trained computer vision classification system, the trained computer vision classification system being built based on transfer learning applied to a pretrained computer vision model trained using training data including a subset of the visual image representations of the plurality of wine samples, each visual image representation in the training data associated with at least one identified classification;
receiving an indication of a selection of one or more of the visual image representations of the plurality of wine samples other than the subset of the visual image representations in the training data; and
executing the trained computer vision classification system using the selected one or more visual image representations of the plurality of wine samples to generate an output including an indication of whether the selected one or more visual image representations of the plurality of wine samples corresponds to the at least one identified classification.

14. The system of claim 13, wherein the infrared spectroscopy includes Fourier transform infrared spectroscopy.

15. A system comprising:
a processor;
a storage device; and a memory in communication with the processor, the memory storing program instructions, the processor operative with the program instructions to perform the operations of:

generating, by infrared spectroscopy, spectra data identifying quantities and associated wavelengths of radiation absorption for each of a plurality of wine samples as determined by the infrared spectroscopy;

converting the spectra data for each wine sample to a set of discretized data;

transforming the discretized data into a visual image representation of each respective wine sample, the visual image representation of each wine being an optically recognizable representation of the corresponding converted set of discretized data;

building a trained computer vision classification system, the trained computer vision classification system being built based on transfer learning applied to a pretrained computer vision model trained using training data including a subset of the visual image representations of the plurality of wine samples, each visual image representation in the training data being associated with at least one categorical quality;

receiving an indication of a selection of one or more of the visual image representations of the plurality of wine samples other than the subset of the visual image representations in the training data; and executing the trained computer vision classification system using the selected one or more visual image representations of the plurality of wine samples to generate an output including an indication of a predicted flavor profile correspondence of the selected one or more visual image representations of the plurality of wine samples with the at least one categorical quality.

16. The system of claim 15, wherein the at least one categorical quality associated with each visual image representation in the training data is provided by at least one of a machine-based expert system and a human.

17. The system of claim 15, wherein the at least one categorical quality includes one or more environmental perturbations, one or more marketing key performance indicators, and one or more other types of categorical assignments related to wine.

18. The system of claim 15, wherein the at least one categorical quality includes one or more different user wine preferences and wherein the trained computer vision classification system is executed using the selected one or more visual image representations of the plurality of wine samples to generate an output including an indication of whether the selected one or more visual image representations of the plurality of wine samples corresponds to a user flavor profile consistent with the one or more different user wine preferences.

* * * * *